United States Patent [19]
Simon et al.

[11] Patent Number: 5,882,658
[45] Date of Patent: Mar. 16, 1999

[54] COMPOSITION FOR COMBATTING SKIN BLEMISHES AND/OR AGEING OF THE SKIN, AND USES THEREOF

[75] Inventors: Pascal Simon, Sur Seine; Didier Gagnebien, Chatillon, both of France

[73] Assignee: L'Oreal, Paris, France

[21] Appl. No.: 685,983

[22] Filed: Jul. 22, 1996

[30] Foreign Application Priority Data

Jul. 20, 1995 [FR] France .................................. 95 08816

[51] Int. Cl.$^6$ ...................................................... A61K 6/00
[52] U.S. Cl. ...................... 424/401; 424/195.1; 514/844; 514/938
[58] Field of Search ................ 424/401, 195.1; 514/844, 938

[56] References Cited

U.S. PATENT DOCUMENTS

| | | | |
|---|---|---|---|
| 4,814,346 | 3/1989 | Albert et al. | 514/454 |
| 5,043,323 | 8/1991 | Bombardel et al. | 514/25 |
| 5,084,563 | 1/1992 | Sakai | 536/41 |
| 5,443,839 | 8/1995 | Meybeck | 424/450 |
| 5,494,667 | 2/1996 | Uchida | 424/195.1 |

FOREIGN PATENT DOCUMENTS

| | | |
|---|---|---|
| 0 425 066 A1 | 5/1991 | European Pat. Off. . |
| 0 461 827 A3 | 12/1991 | European Pat. Off. . |
| 487404-A1 | 5/1992 | European Pat. Off. . |
| 2 680 466 | 2/1993 | France . |
| 43 39 486 A1 | 5/1995 | Germany . |
| 01096125 | 4/1989 | Japan . |
| 01096126 | 4/1989 | Japan . |
| 05213736-A | 8/1993 | Japan . |

OTHER PUBLICATIONS

Helmut W. Xchmalle et al., "Aspects of the Relationships Between Chemical Structure and Sensitizing Potency of Flavonoids and Related Compounds", Plant Flavonoids in Biology and Medicine: Biochemical, Pharmacological, and Structure–Activity Relationships, pp. 387–390, 1986.

Jadwiga Robak et al., "Flavonoids are Scavengers of Superoxide Anions", Biochemical Phamacology, vol. 37, No. 5, pp. 837–841, 1988.

M.J. Alcaraz et al., "Flavonoids as Anti–Inflammatory Agents", Fitoterapia, vol. LIX, No. 1, 1988.

*Primary Examiner*—D. Gabrielle Brouillette
*Attorney, Agent, or Firm*—Oblon, Spivak, McClelland, Maier & Neustadt, P.C.

[57] ABSTRACT

The invention relates to a composition which makes it possible, in particular, to combat photo-induced ageing of the skin and/or to combat skin blemishes, this composition containing, in a cosmetically and/or dermatologically acceptable medium, at least one saccharide ester of ascorbic acid and at least one saccharide ester of rutin, the phase of this medium having a pH of from 4 to 6.

14 Claims, No Drawings

COMPOSITION FOR COMBATTING SKIN BLEMISHES AND/OR AGEING OF THE SKIN, AND USES THEREOF

BACKGROUND OF THE INVENTION

1. Field of the Invention

The invention relates to a composition containing rutin and ascorbic acid derivatives as well as methods for depigmenting skin, preventing or combating skin blemishes and preventing or combating ageing of skin. This composition may be applied to the face, body, neck, hands or legs.

2. Description of the Background

Over the course of time, various signs appear on the skin which are very characteristic of ageing. In particular, the structure and functions of the skin are modified. This ageing is physiological in nature but may also be photoinduced due to repeated exposure of the skin to sunlight, in particular ultraviolet light.

The action of this light on the constituents of the skin and on the sebum secreted by the skin leads to the formation of oxygen-containing free radicals. These radicals cause considerable damage in cell membranes (permeability of the membranes), cell nuclei (mutation by action on RNA or DNA) and tissues (necroses, degeneration). Thus, the skin should be protected against these free radicals.

The main clinical signs of ageing of the skin are the appearance of fine lines and deep wrinkles which increase with age, as well as a disorganization of the "grain" of the skin (i.e., the skin microrelief is less uniform and is anisotropic in nature). Moreover, the skin complexion is generally modified and appears yellowed, which essentially is due to a disorganization of the microcirculation (less haemoglobin in the papillary dermis). Furthermore, many colored and/or darker marks appear at the skin surface and, in particular, on the hands, imparting non-uniformity to the skin. In general, these marks are due to an appreciable production of melanin in the skin epidermis and dermis. In certain cases of intense exposure to solar rays, these marks may become cancerous. Moreover, diffuse irritations and occasionally telangiectasias may exist on certain areas of the skin.

Another clinical sign of ageing is the dry and rough appearance of the skin, which is due essentially to pronounced desquamation caused by diffracting light rays. These squama also contribute towards the somewhat grayish appearance of the complexion. Thus, the clinical signs of skin ageing result essentially from dysfunction of the main biological mechanisms involved in the skin.

Also, certain people with colored skin seek to reduce their color by using depigmenting and/or anti-pigmenting agents.

Thus, a composition which is capable of preventing and/or combating the onset of ageing and the existing signs of ageing, more especially photoinduced ageing, such as wrinkles and fine lines, which is capable of depigmenting the skin and of preventing and/or combating skin pigmentation marks irrespective of their origin, and which is capable of protecting the skin in particular by suppression of the formation of oxygen-containing free radicals is desirable.

One of the effective known means for combating premature ageing of the skin consists in supplying the skin with molecules capable of helping the cells defend themselves against the excess of photoinduced free radicals. Molecules having a hydrophilic, strong reductive power which react with free radicals such as peroxide, superoxide and hydroxyl radicals are especially useful.

One of these molecules capable of effectively combating these free radicals and thus of strengthening the defenses of skin tissue against external attack (ultraviolet radiation, pollution) is ascorbic acid, or vitamin C, on account of its antioxidant properties. This compound also compensates for the deficiency of vitamin E, by stimulating the synthesis of connective tissue and, in particular, skin collagen, and depigmenting the skin.

Unfortunately, on account of its chemical structure and its reductive properties, ascorbic acid is very sensitive to certain environmental parameters such as light, oxygen and water (owing to its pH and the presence of traces of metals). As the rapid degradation of ascorbic acid ensues, it loses its properties, counteracting the desired effect. This degradation results in a yellow/brown color in the composition containing it.

In order to reduce and delay the degradation of ascorbic acid, researchers have attempted to block the reactive site of ascorbic acid, namely the hydroxyl site, by esterification with a saccharide. For example, ascorbyl-2-glucoside is described in document EP-A-487,404 and has the advantages of being more stable than vitamin C, having good water solubility and being bioconvertible into vitamin C on the skin by means of certain skin enzymes, thereby allowing all the properties of vitamin C to be regained.

On account of its good water solubility, this compound may be incorporated into a large number of excipients. However, its stability in an aqueous medium, and in particular in an oil-in-water emulsion, is good (longer than 14 days) only if the pH was above 6. However, the stability of cosmetic compositions at room temperature must be longer than several months, in particular since no expiration date for the products is indicated on the packaging.

The following table shows the stability of 2-ascorbyl glucoside over time and as a function of the pH.

TABLE

| Storage Stability | Day 0 | 14 days without light | 14 days in light | 30 days in light | 60 days in light |
|---|---|---|---|---|---|
| pH of the aqueous solution | 2.2 | 2.18 | 2.27 | 2.1 | 2.48 |
| % residual ascorbyl-2-glucoside | 12.3% | 11.8% | 11.6% | 10.4% | 9.3% |
| Stability (residual %/initial %) | 100% | 95.9% | 94.3% | 84.5% | 75.6% |
| pH of the aqueous solution | 2.7 | 2.7 | 2.8 | 2.59 | 2.59 |
| % residual ascorbyl-2-glucoside | 0.58% | 0.57% | 0.57% | 0.51% | 0.47% |
| Stability (residual %/initial %) | 100% | 98.3% | 98.3% | 87.9% | 81% |
| pH (citrate/phosphate buffer) | 4 | 3.98 | 3.78 | 3.74 | 3.86 |
| % residual ascorbyl-2-glucaside | 0.6% | 0.6% | 0.58% | 0.54% | 0.49% |
| Stability (residual %/initial %) | 100% | 100% | 96.7% | 90% | 81.7% |
| pH (citrate/phosphate buffer) | 6 | 6.04 | 5.96 | 5.91 | 6.21 |
| % residual ascorbyl-2-glucoside | 0.59% | 0.61% | 0.6% | 0.61% | 0.59% |
| Stability (residual %/initial %) | 100% | 103.4% | 101.7% | 103.4% | 100% |
| pH (borate buffer) | 8 | 7.9 | 7.53 | 7.54 | 7.79 |
| % residual ascorbyl-2-glucoside | 0.61% | 0.62% | 0.62% | 0.61% | 0.59% |
| Stability (residual %/initial %) | 100% | 101.6% | 101.6% | 100% | 96.7% |

From this table, it is clear that the stability of 2-ascorbyl glucoside is enhanced when the pH is above 6. This stability at pH>6 holds true for other saccharide esters of ascorbic acid.

Other molecules with antioxidant properties which are known are flavonoids. These compounds have the advantage of being anti-inflammatory agents as well as anti-superoxide anion agents. More generally, they are effective in deactivating radical species of oxygen. These properties are described in documents U.S. Pat. No. 5,043,323, U.S. Pat. No. 5,443,839, U.S. Pat. No. 4,814,346, JP-A-01096125, JP-A-01096126 and in the articles "Flavonoids as antioxidants evaluated by in vitro and in situ liver chemiluminescence" by C. G. Fraga et al., Biochemical Pharmacology, vol. 36, No. 5, 1987, pp. 717–720; "Flavonoids as anti-inflammatory agents" by M. J. Alcaraz and M. J. Jimenez, Fitoterapia, vol. LIX, No. 1, 1988, pp. 25–38; and "Flavonoids are scavengers of superoxide anions" by J. Robak and R. J. Gryglewski, Biochemical Pharmacology, vol. 37, No. 5, 1988, pp. 837–841; all incorporated herein by reference.

Unfortunately, most of these flavonoids are sensitizing compounds which can cause allergic reactions when they are applied to the skin. In contrast, rutin is a flavonoid which has a zero score in the FCA method (maximized test with Freud adjuvant, as described in the article "Aspects of the relationships between chemical structure and sensitizing potency of flavonoids and related compounds" by H. W. Schmalle et al., Prog. Clin. Biol. Res., vol. 213, 1986, pp. 387–390). Unfortunately, rutin is very sparingly water-soluble (about 0.01%).

In contrast, saccharide esters of rutin such as alpha-glycosyl rutin are water soluble and, in addition, are bioconvertible on contact with skin enzymes and have better light stability than rutin. However, alpha-glycosyl rutin gives a yellow solution in water; the intensity of the color depends on the pH. If the pH is below or equal to 5, the yellow color is of weak intensity, from virtually colorless to pale yellow, and is stable over time. If the pH is above 5, the color becomes increasingly intense and ranges from dark yellow to brown depending on the percentage of alpha-glucosyl rutin. In this case, the composition becomes cosmetically unacceptable, not only due to its color but also because the color changes over time.

In other words, ascorbyl-2-glucoside and, more generally, saccharide esters of ascorbic acid are unstable at pH values below 5. Alpha-glycosyl rutin and, more generally, saccharide esters of rutin color excipients containing them at pH values above 5 in such a manner as to make them unacceptable.

SUMMARY OF THE INVENTION

One object of the present invention is to provide a stable composition for topical skin application, which has a high protective power against photoinduced radicals.

A second object it to provide methods for preventing and/or combatting extrinsic and intrinsic skin blemishes and/or ageing of the skin.

Thus, the present Applicants have discovered, surprisingly, that the saccharide derivatives of ascorbic acid are entirely compatible with the saccharide esters of rutin and that they can be formulated in any type of excipient containing water at pH 4–6. These derivatives have the advantage, in particular, of being very water-soluble and of not modifying the physical and chemical properties of these saccharide esters of rutin.

According to an essential characteristic of the invention, this composition contains an aqueous phase, having a pH in the range from 4 to 6, which contains at least one saccharide ester of ascorbic acid and at least one saccharide ester of rutin.

DETAILED DESCRIPTION OF THE PREFERRED EMBODIMENTS

The present invention provides a composition in which a saccharide ester of ascorbic acid and a saccharide ester of rutin are stable by selecting a pH in the range from 4 to 6. It is entirely surprisingly that ascorbyl-2-glucoside, in particular, remains stable at this pH and that the color of the composition does not change over time. In particular, ascorbyl-2-glucoside is still not degraded after 12 months at room temperature (about 25° C.) and alpha-glucosyl rutin remains very stable in this medium since the pale yellow color of the composition does not change.

Suitable saccharide esters of ascorbic acid which can be used in the invention include glucosyl, mannosyl, fructosyl, fucosyl, galactosyl, N-acetylglucosamine and N-acetylmuramic derivatives of ascorbic acid and mixtures thereof. Preferred saccharide esters of ascorbic acid include ascorbyl-2-glucoside, 2-O-α-D-glucopyranosyl L-ascorbate, or 6-O-β-D-galactopyranosyl L-ascorbate. The latter compounds and their manufacture are described in particular in documents EP-A-487,404, U.S. Pat. No. 5,084, 563 and J05213736; incorporated herein by reference.

A suitable amount of saccharide derivatives of ascorbic acid is, for example, from 0.01 to 20% by weight relative to the total weight of the composition, preferably from 0.01 to 10% and, more preferably, from 0.5 to 5%. Furthermore, the composition may contain one or more saccharide derivatives.

Suitable saccharide esters of rutin in include glucosyl, mannosyl, fructosyl and fucosyl derivatives of rutin and mixtures thereof, preferably alpha-glucosyl rutin.

A suitable amount of saccharide ester of rutin which can be used is that generally used in the fields concerned. In practice, from 0.001 to 5% by weight is used relative to the total weight of the composition, preferably from 0.01 to 1% and, more preferably, from 0.01 to 0.5%. Furthermore, the composition may contain one or more saccharide esters of rutin.

The composition may advantageously contain a cosmetically and/or dermatologically acceptable medium which is compatible with the skin, including the scalp, hair and nails.

The composition may advantageously be in any pharmaceutical form normally used for topical application, which contains water, such as solutions, aqueous or aqueous-alcoholic gels, oil-in-water or water-in-oil emulsions and, more particularly, droplets of oil dispersed by spherules in an aqueous phase. The composition of the invention may be in the form of a cream, an ointment, a lotion or a serum.

Suitable spherules may be polymer nanoparticles such as nanospheres and nanocapsules, preferably lipid vesicles containing ionic or nonionic lipids.

Suitable oils which may be used in the invention are those generally used in the fields concerned. They may be vegetable (such as sunflower oil, apricot oil, karite butter), mineral (such as liquid paraffin, isohexadecane) or synthetic (such as isopropyl palmitate, myristyl myristate, hydrogenated paraffin) oils and optionally silicone-containing cyclohexadimethylsiloxane, cyclopentadimethylsiloxane) and/or fluoro oils (such as perfluoropolyethers).

Suitable amounts of oil and water are generally those used in the fields in question and depend on the pharmaceutical form of the composition. For an oil-in-water emulsion or a dispersion of oil in water by means of liquid spherules, the oil may represent from 2 to 40% by weight relative to the total weight of the composition.

To enhance protection against free radicals, it is possible to add other antioxidant and/or anti-radical molecules to the composition such as iron-chelating agents (such as EDTA), anti-lipo-peroxide agents (such as vitamin E and derivatives), compounds for regenerating oxidized vitamin E (such as vitamin C), anti-hydroxyl-radical agents (such as gingko biloba, caffeine), anti-singlet-oxygen agents (such as ethoxyquine) and anti-superoxide-anion-radical agents (such as superoxide dismutase) and combinations thereof, as well as UVA (such as terephthalylidene dicamphor sulfonic acid) and/or UVB (such as Parasol MCX) screening agents.

The invention may also contain hydrophilic or lipophilic adjuvants such as gelling agents (such as xanthan gum, alkyl carboxyvinyl polymer, carboxyvinyl polymer), preserving agents (such as methyl- or ethyl-p-hydroxybenzoate), opacifiers (such as talc, starch), emulsifiers (such as polyethylene glycol stearate (40 OE), glyceryl mono-, di- and tripalmitostearate), co-emulsifiers (such as cetyl alcohol, stearyl alcohol), fragrances and solubilizing (such as alkylbenzoate, alcohols and glycols) or peptizing agents thereof (such as oxyethylenated hydrogenated ricinoleic triglycerides (60 OE), dyes, pigments, fillers and lipophilic or hydrophilic active agents other than the saccharide esters of ascorbic acid and of rutin. A peptizing agent is an agent which solubilizes a fragrance.

The adjuvants are used in the conventional amounts and may represent, in total, from 0.1 to 20% by weight. Their amount depends on their nature.

The compositions of the present invention are stable at 25° C. for at least 6 months, preferably at least 12 months.

The composition of the invention may be applied topically to any part of the body and face, including the scalp, the legs and the hands. The composition is especially useful for application to human skin.

The subject of the invention is also a method for the treatment of the signs of ageing of the skin and, in particular, wrinkles and/or fine lines on the skin. The subject of the invention is also a method for depigmenting the skin, to prevent and/or combat skin blemishes due in particular to ageing. The methods comprise applying the composition of the present invention to skin. The invention also relates to a method for protect the skin against free radicals by applying the composition of the present invention to skin.

Other characteristics and advantages of the invention will emerge more clearly from the description which follows, which is given by way of illustration and with no limitation implied. In the following examples of cosmetic and/or dermatological compositions in accordance with the invention, the amounts are given as a % by weight.

Having generally described this invention, a further understanding can be obtained by reference to certain specific examples which are provided herein for purposes of illustration only and are not intended to be limiting unless otherwise specified.

EXAMPLES

Example 1

Oil-in-water cream for preventing pigmentation of the skin

| Composition | | |
|---|---|---|
| A1 | Stearic acid | 0.4% |
|  | Polyethylene glycol stearate | 3.5% |
|  | (40 EO) (emulsifying agent) |  |
|  | Cetyl alcohol (co-emulsifying agent) | 3.2% |
|  | Glyceryl mono-, di- and tripalmito-stearate (emulsifying agent) | 3.0% |
|  | Myristyl myristate (oil) | 2.0% |
|  | Isopropyl palmitate (oil) | 7.0% |
|  | Hydrogenated isoparaffin (6–8 mol of isobutylene) (oil) | 6.5% |
| A2 | Cyclopentadimethylsiloxane (oil) | 5.0% |
| B | Demineralized water | qs 100% |
|  | Glycerol (moisturizing agent) | 3.0% |
|  | Ascorbyl-2-glucoside sold by Hayashibara | 2.0% |
|  | Alpha-glycosyl rutin | 0.2% |
|  | Preserving agent | 0.2% |

Preparation of phase A1+A2

The constituents of A1 are solubilized at 80° C. When the mixture is clear, the temperature is lowered to 65° C. and A2 is added. The mixture must be clear and homogeneous. The temperature of 65° C. is maintained.

Manufacture

The constituents of B are solubilized at 85° C.–90° C. in a production beaker. After checking that the solution is clear, the temperature is cooled to 65° C. The emulsion is prepared, with stirring, by pouring (A1+A2) into B. Cooling is continued, with stirring, to room temperature.

A white skin-care cream for daily protection of the skin against the harmful effects of UV radiation and for preventing the formation of photoinduced wrinkles and fine lines is obtained.

Example 2

Gel for protecting against solar rays

| Composition | | |
|---|---|---|
| A | Demineralized water | qs 100% |
|  | Glycerol | 3.0% |
|  | Methyl para-hydroxybenzoate | 0.2% |
|  | Ascorbyl-2-glucoside | 1.0% |
|  | Alpha-glycosyl rutin | 0.05% |
|  | Xanthan gum (thickener) | 0.2% |
| B | Parsol MCX (UVB screening agent) | 4.0% |
|  | Alkylbenzoate (Finsolv TN, Witco company) | 4.0% |
|  | Alkyl carboxyvinyl polymer (Pemulen TR 2, Goodrich company) | 0.45% |
|  | Triethanolamine | 0.45% |

Manufacture

Phase A is prepared by sprinkling the gelling agent into the water containing the dissolved ingredients, while stirring. The mixture is emulsified by incorporating phase B into phase A, with vigorous stirring. The mixture is mixed until smooth and left to cool, with slow paddle stirring, at room temperature. Manufacture of the gel is complete.

Example 3

"Clear complexion" lotion

| Composition | | |
|---|---|---|
| A | Oxyethylenated hydrogenated ricinoleic triglycerides (60 EO) (peptizing agent) | 0.09% |
|  | Fragrance | 0.03% |

-continued

| Composition | | |
|---|---|---|
| B | Demineralized water | qs 100% |
| | Ascorbyl-2-glucoside | 1.0% |
| | Alpha-glycosyl rutin | 0.05% |
| | Preserving agent | 0.3% |

Manufacture

The constituents of A are mixed together at 40° C. When they are fully solubilized, the constituents of B are added in sequence at room temperature. Stirring is continued and correct solubilization of the constituents is confirmed; the mixture must be clear. Manufacture is complete.

A clear lotion for preventing and reducing pigmentation of the skin is obtained.

Having now fully described the invention, it will be apparent to one of ordinary skill in the art that many changes and modifications can be made thereto without departing from the spirit or scope of the invention as set forth herein.

This application is based on application No. 95-08816 filed in France on Jul. 20, 1995. The full text of this foreign application is incorporated herein by reference.

What is claimed as new and is desired to be secured by Letters Patent of the United States is:

1. A composition comprising an aqueous solution of at least one saccharide ester of rutin and at least one saccharide ester of ascorbic acid, having a pH of from 4 to 6.

2. The composition of claim 1, wherein the saccharide ester of rutin is alpha-glycosyl rutin.

3. The composition of claim 1, wherein the saccharide ester of ascorbic acid is ascorbyl-2-glucoside.

4. The composition of claim 1, which further comprises an oil phase such that said composition is an oil-in-water emulsion.

5. The composition of claim 1, which further comprises lipid spherules.

6. The composition of claim 1, wherein the saccharide ester of ascorbic acid is from 0.01 to 20% by weight, relative to the total weight of the composition.

7. The composition of claim 1, wherein the saccharide ester of rutin is from 0.001 to 5% by weight, relative to the total weight of the composition.

8. The composition of claim 1, which further comprises hydrophilic or lipophilic adjuvants.

9. The composition of claim 1, which further comprises a cosmetically or dermatologically acceptable medium.

10. A method of treating the signs of ageing of the skin, which comprises:

applying to the skin a composition comprising an aqueous solution of at least one saccharide ester of rutin and at least one saccharide ester of ascorbic acid, wherein the pH of the solution is from 4 to 6, said signs of ageing being wrinkles and fine lines in the skin.

11. A method of depigmenting the skin, which comprises applying to skin a composition comprising an aqueous solution of at least one saccharide ester of rutin and at least one saccharide ester of ascorbic acid, wherein the pH of the solution is from 4 to 6.

12. A method of protecting the skin against free radicals, which comprises applying to skin a composition comprising an aqueous solution of at least one saccharide ester of rutin and at least one saccharide ester of ascorbic acid, wherein the pH of the solution is from 4 to 6.

13. The composition of claim 1, which further comprises at least one anti-oxidant selected from the group consisting of iron-chelating agents, anti-lipo-peroxide agents, compounds which regenerate oxidized vitamin E, anti-hydroxyl-radical agents, anti-singlet-oxygen agents, anti-superoxide-anion-radical agents and UVA and UVB screening agents.

14. The composition of claim 8, wherein said adjuvants are gelling agents, preserving agents, opacifiers, emulsifiers, co-emulsifiers, fragrances, solubilizing agents, peptizing agents, dyes, pigments and fillers.

* * * * *